United States Patent [19]

Mizuno

[11] Patent Number: 5,309,186
[45] Date of Patent: May 3, 1994

[54] EYE REFRACTIVE POWER MEASURING APPARATUS HAVING OPACITY DISCRIMINANT FUNCTION OF CRYSTALLINE LENS

[75] Inventor: Toshiaki Mizuno, Aichi, Japan

[73] Assignee: Nidek Co., Ltd., Gamagori, Japan

[21] Appl. No.: 826,789

[22] Filed: Jan. 28, 1992

[30] Foreign Application Priority Data

Jan. 30, 1991 [JP] Japan .................................. 3-29417

[51] Int. Cl.⁵ .......................... A61B 3/14; A61B 3/10
[52] U.S. Cl. ................................... 351/212; 351/206; 351/211
[58] Field of Search ............... 351/206, 208, 211, 214, 351/221, 243, 247; 354/62

[56] References Cited

U.S. PATENT DOCUMENTS

| | | | |
|---|---|---|---|
| 4,376,573 | 3/1983 | Matsumura et al. | 351/211 |
| 4,711,540 | 12/1987 | Yoshino et al. | 351/214 |
| 4,744,648 | 5/1988 | Kato et al. | 351/211 |
| 4,755,041 | 7/1988 | Ishikawa et al. | 351/211 |
| 4,917,480 | 4/1990 | Kato et al. | 351/211 |
| 5,202,708 | 4/1993 | Sasaki et al. | 351/200 |

*Primary Examiner*—Loha Ben
*Assistant Examiner*—Thong Nguyen
*Attorney, Agent, or Firm*—Finnegan, Henderson Farabow, Garrett & Dunner

[57] ABSTRACT

An eye refractive power measuring apparatus having an opacity discriminant function of a crystalline lens comprising a projecting optical system for projecting a target for eye refractive power measurement onto a fundus of an eye to be examined, a detecting optical system for detecting the target image reflected from the eye fundus, a device coupled to the detecting optical system for measuring refractive power of the eye in response to the detected target image, an irradiating optical system for irradiating the eye fundus with a retroillumination light, and an observing optical system for observing a crystalline lens of the eye illuminated by the retroillumination light reflected from the eye fundus to determine the opacity of the crystalline lens.

16 Claims, 2 Drawing Sheets

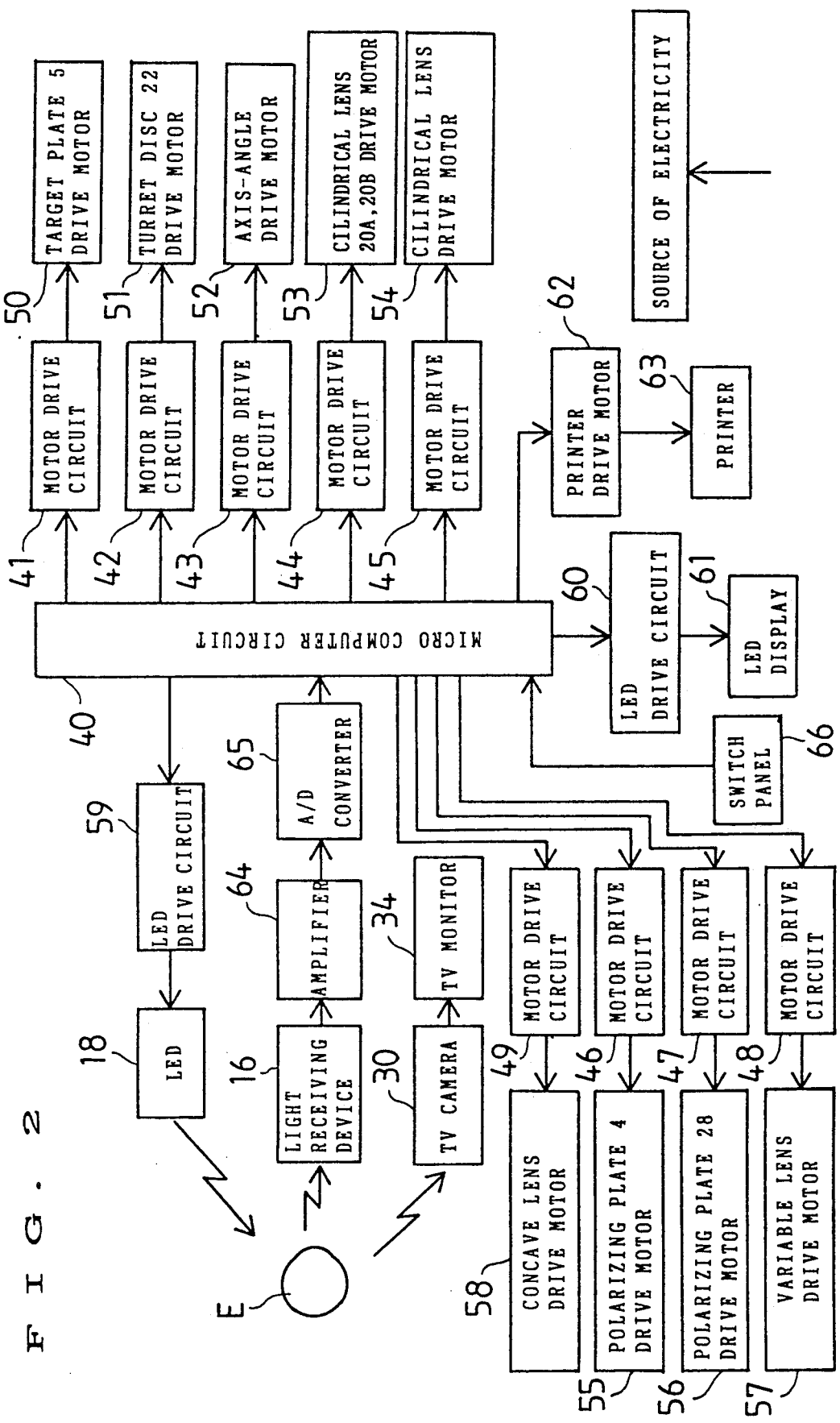

EYE REFRACTIVE POWER MEASURING APPARATUS HAVING OPACITY DISCRIMINANT FUNCTION OF CRYSTALLINE LENS

BACKGROUND OF THE INVENTION

1. Field of the Invention

The present invention relates to an apparatus for measuring the refractive power of an eye to be examined objectively. More particularly, the present invention relates to an eye refractive power measuring apparatus having the ability to discriminate the lens opacity of an eye.

2. Description of Related Art

Conventionally, some eye refractive power measuring devices are known which can measure the refractive power of the spherical surface, cylindrical surface, cylindrical axis, and so on of an eye to be examined objectively. Both hand-operated types and auto-operated types have been available, but the auto-operated type is now broadly used. The auto-operated type was first utilized about twenty years ago, and because of several improvements is now a high-accuracy apparatus.

The eye refractive power measuring devices measure the refractive power by projecting a target onto the fundus of an eye to be examined and receiving a reflection from the fundus by a light receiving device (an image sensor etc.). These devices have only been able to measure the refractive power properties of the eye, and factors such as the lens opacity of the eye which affect the light reflected from the eye fundus have usually been overlooked. However, it is necessary to consider the lens opacity and its influence on eyesight under special sight circumstances.

If the lens opacity of the eye to be examined is so great that the measuring light cannot reach to the fundus, prior devices have not been able to determine whether or not the reason is the lens opacity. Such devices have only indicated that it is impossible to measure the eye refractive power. Moreover, in the case of adjusting the prescription for glasses, although a subjective measurement will be taken by using visual charts and a lens system after completing the objective measurement, if the lens opacity is not clearly indicated, the cause of a difference between the objective measurement value and the subjective measurement value may not be known.

SUMMARY OF THE INVENTION

Accordingly, it is an object of the present invention to overcome the above problems and to provide an eye refractive power measuring apparatus having a crystalline lens opacity discriminant function.

Another object of the present invention is to provide an eye refractive power measuring apparatus for detecting early a cause of the failing eyesight other than the errors of refractive power in order to provide a proper treatment.

The above objects and further objects and novel features of the invention are attained by an eye refractive power measuring apparatus having a crystalline lens opacity discriminant function comprising a projecting optical system for projecting a target for eye refractive power measurement onto a fundus of an eye to be examined, a detecting optical system for detecting the target image reflected from the eye fundus, means coupled to said detecting optical system for measuring refractive power of the eye in response to the detected target image, an irradiating optical system for irradiating the eye fundus with a retroillumination light, and an observing optical system for observing a crystalline lens of the eye illuminated by the retroillumination light reflected from the eye fundus to determine the opacity of the crystalline lens.

BRIEF DESCRIPTION OF THE DRAWINGS

The manner by which the present invention can be attained will be fully understood by consideration of the following detailed description when it is considered with reference to the drawings, wherein:

FIG. 2 is a control block diagram for the measuring apparatus embodying the present invention.

DETAILED DESCRIPTION OF THE PREFERRED EMBODIMENTS

Figure 1:
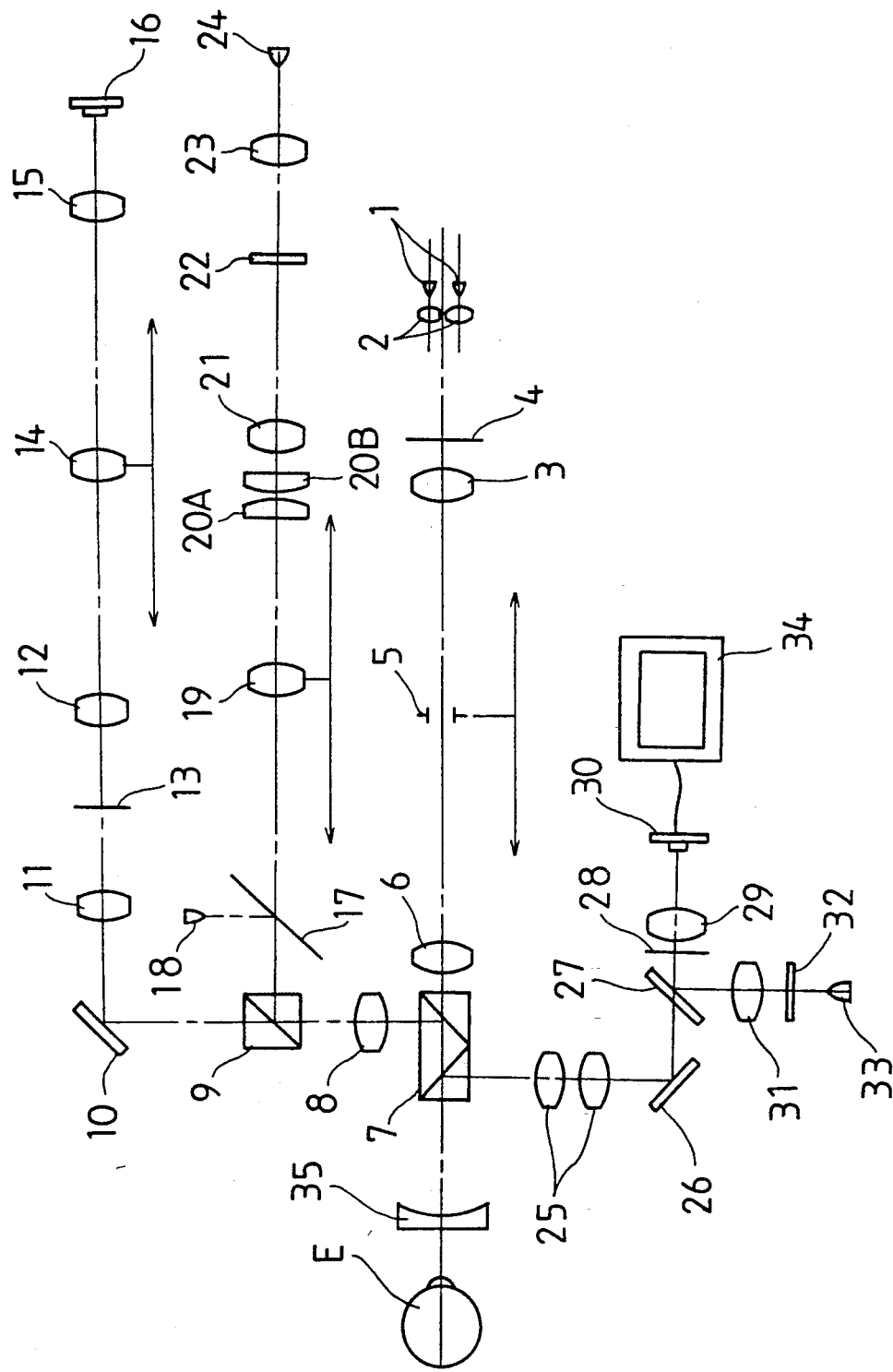
FIG. 1 is a schematic diagram of the optical arrangement of the eye refractive power measuring apparatus embodying the present invention.

A detailed description of one preferred embodiment of an eye refractive power measuring apparatus embodying the present invention will now be given referring to the accompanying drawings.

As shown in FIG. 1, an optical system for an eye refractive power measuring apparatus includes a first projecting optical system for projecting a measurement target onto the fundus of the eye to be examined, a detecting optical system for detecting the target image reflected from the eye fundus, an irradiating optical system for irradiating a retroillumination light onto the eye fundus an observing optical system for observing an image of the crystalline lens retroilluminated by the reflected light from the eye fundus, a second projecting optical system for projecting a fixation target onto the eye fundus, and an alignment optical system.

Projection Optical System for Measuring Eye Refractive Power

The projection optical system for projecting a measurement target onto the fundus of an eye to be examined includes a light source 1 emitting infrared rays, condenser lenses 2,3, a measurement target plate 5 having a target (an aperture) for measuring the eye refractive power, an objective lens 6 to be selected so as to form the magnifying optical system to the fundus image in a position of the measurement target plate 5, and a beam splitter 7. The target plate 5 is movable in the optical path along the optical axis so as to be positionable conjugate with the fundus of the eye E to be examined. Between the condenser lenses 2 and 3 of this optical system, there is disposed a polarizing plate 4 to polarize light emitted from the light source 1. This polarizing plate 4 may be moved out of the optical path at the time of measuring the eye refractive power.

At the time of measuring the eye refractive power, the light emitted from the light source 1 passes through the spot aperture (the target for measuring an eye refractive power) of the target plate 5 via the condenser lenses 2,3, and is directed to the fundus of the eye E via the objective lens 6 and the beam splitter 7. On this occasion, the light, after being focussed near the cornea, is transmitted to the fundus of the eye E.

Detecting Optical System

The detecting optical system includes an objective lens 8, a beam splitter 9, a reflecting mirror 10, relay lenses 11,12, a cornea reflecting rejection mask 13, a movable lens 14, a focussing lens 15, and a light receiving device 16. These components are disposed in the optical path of the light reflected from the eye fundus. The reflected light is divided by the beam splitter 7 after being projected onto the fundus of the eye E via the first projection optical system.

The cornea reflecting rejection mask 13 is disposed in the optical path to be conjugate with the cornea of the eye E to be examined. The movable lens 14 is disposed in the optical path to be movable along the optical axis, and it also moves synchronously with the movement of the target plate 5 of the first projection optical system. The amount of the movement has a relation with the eye refractive power value. The light receiving device 16 is rotated around the optical axis synchronously with the light source 1, the condenser lenses 2,3, and the cornea reflecting rejection mask 13.

Irradiating Optical System

In this embodiment, the irradiating optical system for observing the retroillumination image and the first projection optical system are employed in common. But when observing the retroillumination image, the polarizing plate 4 is inserted in the optical path.

Observing Optical System

The observing optical system includes a pair of variable lenses 25, a reflecting mirror 26, a dichroic mirror 27, a polarizing plate 28, a focussing lens 29, and an imaging device 30. The light reflected by the fundus or the anterior portion of the eye E is divided by the beam splitter 7 for observing the retroillumination image or the anterior portion.

The variable lenses 25 are selectively insertable in the optical path, and are used to raise the image magnification by inserting them in the optical path when observing the retroillumination image. The phase angle of the polarizing plate 28 differs 90° with respect to that of the polarizing plate 4. The polarizing plate 28 is also selectively insertable in the optical path, and is inserted into the optical path when observing the retroillumination image.

In the present embodiment, a television monitor 34 is connected to the imaging device 30 to display the image received by the imaging device 30.

A convex lens 35 is also selectively insertable in the optical path between the eye E and the beam splitter 7 and is inserted into the optical path only when observing the retroillumination image, whereby the light for observing the retroillumination image is incident on the eye E as a parallel light beam. In this embodiment, the eye refractive power measurement method, wherein a target image projected by the light source 1 for measuring eye refractive power is formed near the cornea, is employed for observing the retroillumination image. Therefore, even though there is an obstacle at the focal point, it is cancelled from the retroillumination image by using the convex lens 35.

Projection Optical System for Fixation Target

The second projection optical system for projecting a fixation target onto the fundus includes an illumination lamp 24, a turret disc 22, which provides some changeable fixation targets such as for objective measurement, eye sight measurement, retroillumination image observation, and so on, first and second relay lenses 19, 21, a dichroic mirror 17, the beam splitter 9, the objective lens 8, and the beam splitter 7.

The turret disc 22 is disposed in the optical path at the focus position of the second relay lens 21. The first relay lens 19 is movable along the optical axis, and the amount of the movement is in proportion to the spherical power of the eye E to be examined.

In the second projection optical system for the fixation target, correction optical means is provided for correcting errors of refraction of an eye E to be examined. The correction optical means consists of a pair of positive cylindrical lenses 20A, 20B, having equal focus distances. The lenses 20A, 20B are disposed rotatably around the optical axis to move in the same direction or a reverse direction by the same amount. It is necessary to provide a cylindrical correction by the two cylindrical lenses 20A, 20B considering the spherical power.

Alignment Optical System

As an aiming light, a light emitting diode (LED) 18 is employed. The light emitted from the LED 18 is reflected by the dichroic mirror 17, and is incident on the fundus of the eye E via the beam splitter 9, the objective lens 8, and the beam splitter 7. The reflected beam from the fundus is received by the imaging device 30 via the bean splitter 7, the reflecting mirror 26, the dichroic mirror 27, and the focussing lens 29.

On the other hand, the alignment optical system includes a reticule projection light source 33, a reticule plate 32, a relay lens 31, and the dichroic mirror 27, the focussing lens 29, and the imaging device 30. Alignment is achieved by positioning at a predetermined relation a luminance point formed by the light beam from the LED 18 and a reticule image projected by the light from the reticule projection light source 33 while observing the anterior portion of the eye illuminated by an illumination light (not shown) on the television monitor 34 connected to the imaging device 30.

As shown in FIG. 2, a drive motor 50 for the target plate 5, a fixation target drive motor 51 for the turret disc 22, an axis-angle drive motor 52 for the light source 1, the cornea reflecting rejection mask 13, and the light receiving device 16 to be rotated around the optical axis, a reverse rotation drive motor 53 for the cylindrical lenses 20A, 20B to be rotated in the reverse direction around the optical axis with respect to each other for astigmatism correction, a drive motor 54 for the cylindrical lenses 20A, 20B to be rotated in the same direction around the optical axis with respect to each other for astigmatism correction, a drive motor 55 for inserting the polarizing plate 4 into the optical path, a drive motor 56 for inserting the polarizing plate 28 into the optical path, a drive motor 57 for inserting the variable lenses 25, 25 into the optical path, and a drive motor 58 for the concave lens 35 are connected to a micro computer circuit 40 via motor drive circuits 41, 42, 43, 44, 45, 46, 47, 48 and 49. The micro computer circuit 40, the LED 18, LED display 61 and a printer 63 are connected via drive circuit 59, 60, and 62.

Signals received from the light receiving device 16 are inputted to the micro computer circuit 40 via an amplifier 64 and A/D converter 65. On a switch panel 66, several kinds of switches are provided, such as for an eye refractive power measurement, subjective measurement, retroillumination image observation, and so on.

Measurement of Eye Refractive Power

First, an examiner selects the proper fixation target of the turret disc 22 and makes a patient view the target. The examiner then observes the anterior portion of the eye illuminated by an illumination light (not shown), and positions at a determined relation the luminance point formed by the light beams from the LED 18 and a reticule image projected by the light from the reticule projection light source 33.

After properly positioning the eye E to be examined, the examiner pushes the button for eye refractive power measurement on the switch panel 66. The infrared rays emitted from the light source 1 pass through the condenser lenses 2, 3, the target plate 5, the objective lens 6, and the beam splitter 7, and after being focussed near the cornea of the eye E, the light reaches the fundus. In the case of a normal eye, the target image is directed along the optical path via the beam splitter 7, and is reflected by the reflecting mirror 10 via the objective lens 8 and the beam splitter 9, and after passing through the relay lenses 11, 12 the target image is focused onto the light receiving device 16 by the focussing lens 15. On the basis of a signal generated in response to the reflection from the fundus being received by the light receiving device 16, the target plate 5 is moved to a position that is conjugate with the fundus of the eye E by the micro computer (CPU), and the movable lens 14 is also moved in synchronism with the target plate 5.

After the fixation target of the turret disc 22 is focussed onto the fundus of the eye E, the examiner moves the first relay lens 19 so that fogging covers only the proper diopter. The examiner then rotates the light source 1, the cornea reflecting rejection mask 13, and the light receiving device 16 around the optical axis by 180°. During the rotation, on the basis of the signal from the light receiving device 16, the target plate 5 and the movable lens 14 are moved, and, on the basis of the amount of the movement, the eye refractive power value on each meridian is known. That is, by making a predetermined treatment to the eye refractive power value on each meridian, the refractive power of the eye is obtained.

After completing the objective measurement, when the examiner pushes the subjective measurement switch, according to the control of the micro computer, so as to correspond to the value obtained by the objective measurement, the cylindrical lenses 20A, 20B rotate with movement of the first relay lens 19. Accordingly, the patient views the target for the subjective measurement at the condition of correcting the refractive power (correcting the errors of refraction) obtained by the objective measurement. In such a manner according to the determined steps, several kinds of subjective measurement take place.

Observation of Retroillumination Image

After completing the refractive power measurement, the examiner pushes the switch for retroillumination image observation. If the switch is pushed, the polarizing plates 4 and 28 are inserted into the optical path, the turret disc 22 is rotated to select a fixation target which center the patient views easily, and the beam intensity of the illumination lamp 24 is decreased to a predetermined level. At that time, the first relay lens 19 and the cylindrical lenses 20A, 20B are moved to the position for correcting the measurement value of the refractive power, therefore, the central fixation becomes easy and the beam intensity of the illumination lamp 24 is decreased within a range so that there is no problem for observation.

If necessary, the examiner again positions the device with respect to the eye E to be examined. The positioning should take place before the variable lenses 25, 25 are inserted into the optical path of the observing optical system. It is possible to position after inserting the variable lense 25, 25 into the optical path, but it is easier to position when the image magnification is small.

Pushing the retroillumination image observing switch causes the variable lenses 25 to be inserted into the optical path of the observing optical system, the LED 18 and the reticule projection light source 33 are turned off, and the light source 1 is turned on. As the polarizing plates 4 and 28 are employed, if the illumination level of the light source 1 is not sufficient, it is better to increase the number of light sources and to turn on the increased number at the time of observation of the retroillumination image.

A light beam from the light source 1 passes through the same route as the eye refractive power measurement and forms an image near the cornea and is then incident on the eye to be examined and reflected at the eye fundus. The light reflected at the fundus retroilluminates the crystalline lens. The crystalline lens retroilluminated by the reflected light is focussed onto the imaging device 30 via the variable lenses 25, the focussed focussing lens 29 and so on and is displayed on the television monitor 34.

Nuclear cataracts and cortical cataracts are two types of cataracts. In the case of a nuclear cataract, suffering is more severe, and the eye refractive power measurement (AR) cannot be measured because a measurement light cannot reach the fundus or a reflecting light from the fundus cannot be detected, therefore, it is concluded that the impossibility of measurement is due to a crystalline lens opacity.

In a case of the cortical cataract, it is possible to measure a eye refractive power (AR), but when making spectacles based on this measurement value, the shading due to the lens opacity cannot be cleared although the eye sight may be corrected. In this case, it may make a difference between an objective measurement value and subjective measurement value, and it may be concluded that the difference between the values is due to the lens opacity.

In a further case that it will be impossible to correct the eye sight although the spectacles are made based on a value of AR without the lens opacity, there is a danger of suffering from a disease other than a crystalline lens.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein. For instance, as a light source for retroillumination image observation it is possible to employ the LED 18 without employing the light source 1 for projecting a target.

What is claimed is:

1. An eye refractive power measuring apparatus having a crystalline lens opacity discriminant function comprising:

a projecting optical system for projecting a target onto a fundus of an eye under examination to measure the refractive power thereof;

a detecting optical system for detecting an image of the target reflected from the eye fundus;

means coupled to said detecting optical system for measuring the refractive power of the eye in response to said detected target image;

an alignment observing optical system for observing the eye when measuring the refractive power thereof;

an irradiating optical system for irradiating the eye fundus with a retroillumination light; and an observing optical system, for observing a crystalline lens of the eye illuminated by the retroillumination light reflected form the eye fundus to determine the opacity of the crystalline lens, including at least one magnification variable lens disposed on an optical path of said reflected retroillumination light;

wherein said alignment observing optical system and said observing optical system for observing crystalline lens are included in an optical system, and the optical system displays selectively the image of the target reflected from the eye fundus for alignment observation and the image of the crystalline lens by selecting a magnification of the variable lens.

2. The apparatus according to claim 1, wherein the irradiating optical system for the irradiating the retroillumination light and the projecting optical system for projecting the target for the eye refractive power measurement include common optical elements.

3. The apparatus according to claim 2, further including polarizing plates selectively insertable in the irradiating optical system for the retroillumination light and the observing optical system for observing the crystalline lens, and means for inserting said polarizing plates at the time of observing a retroillumination image of the crystalline lens.

4. The apparatus according to claim 2, further including a concave lens selectively insertable in the irradiating optical system to irradiate the retroillumination light as substantially parallel light rays at the time of observing a retroillumination image of the crystalline lens.

5. The apparatus according to claim 1, further including a polarizing plate disposed in the observing optical system for rejecting corneal reflections while observing the crystalline lens.

6. The apparatus according to claim 5, wherein the polarizing plate is removably disposed in the optical path of the observing optical system for observing the crystalline lens.

7. The apparatus according to claim 1, further comprising an alignment optical system included with the observing optical system for observing the crystalline lens.

8. The apparatus according to claim 7, wherein the alignment optical system comprises an alignment light source emitting an alignment light, a reticule light source, and alignment control means for positioning in a predetermined position a luminance point formed by a light beam from the alignment light source and a reticule image projected by a light beam from the reticule light source.

9. The apparatus according to claim 1, wherein a concave lens is disposed in the irradiating optical system to irradiate the retroillumination light as parallel light rays into the eye.

10. The apparatus according to claim 1, wherein the projecting optical system includes an infrared light source, said target being movable along an optical axis of the projecting optical system to a position conjugate with the fundus of the eye to be examined, and said detecting optical system including an optical path an a beam splitter to deflect the reflected target image, a movable lens disposed in said optical path of said detecting optical system and movable along an optical axis of said detecting optical system in synchronism with said target, and a light receiving device for detecting light deflected by the beam splitter.

11. The apparatus according to claim 10, wherein the means for measuring refractive power includes means for moving the target and said movable lens in synchronism, the eye refractive power measurement being indicated by an amount of movement of said target and said movable lens.

12. The apparatus according to claim 11, wherein the moving means also rotates the measurement light source and the light receiving device around an optical axis of the detecting optical system.

13. The apparatus according to claim 1, further comprising:

a fixation target projecting optical system for projecting a fixation target onto the fundus of the eye to be examined.

14. The apparatus according to claim 13, wherein the fixation target projecting optical system comprises an illumination lamp for emitting a light beam having a wave length in the visible region for projecting the fixation target and a turret disc mounting the fixation target.

15. The apparatus according to claim 14, further comprising a correction optical means, for correcting an error of the eye under examination, disposed in an optical path of the fixation target projecting optical system.

16. The apparatus according to claim 15, wherein the correction optical means comprises a pair of cylindrical lenses selectively rotatable around an optical axis of the fixation target projecting optical system in a same direction or reverse directions.

* * * * *